United States Patent
Davies et al.

(10) Patent No.: US 8,663,172 B2
(45) Date of Patent: Mar. 4, 2014

(54) MEDICATED MODULE WITH USER SELECTION

(75) Inventors: James Alexander Davies, Warwickshire (GB); Steven Wimpenny, Leamington Spa (GB); Daniel Thomas De Sausmarez Lintell, Rugby (GB); Malcolm Stanley Boyd, Wellesbourne (GB); Naceur Rekaya, Leamington Spa (GB); Simon Lewis Bilton, Leamington Spa (GB); John David Cross, Northhampton (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 18 days.

(21) Appl. No.: 13/376,018

(22) PCT Filed: Jun. 1, 2010

(86) PCT No.: PCT/EP2010/057579
§ 371 (c)(1),
(2), (4) Date: Jan. 25, 2012

(87) PCT Pub. No.: WO2010/139671
PCT Pub. Date: Dec. 9, 2010

(65) Prior Publication Data
US 2012/0136316 A1   May 31, 2012

Related U.S. Application Data

(60) Provisional application No. 61/183,459, filed on Jun. 2, 2009.

(30) Foreign Application Priority Data

Jul. 25, 2009  (EP) ..................... 09009661

(51) Int. Cl.
*A61M 5/00* (2006.01)

(52) U.S. Cl.
USPC ........................... 604/191; 604/187; 604/197

(58) Field of Classification Search
USPC ......... 604/82–83, 85–89, 187, 191–193, 197, 604/205, 264
See application file for complete search history.

(56) References Cited

U.S. PATENT DOCUMENTS

| | | | | |
|---|---|---|---|---|
| 5,695,475 A | * | 12/1997 | Best et al. | 604/198 |
| 6,562,002 B1 | | 5/2003 | Taylor | |
| 7,534,222 B2 | * | 5/2009 | Sugita et al. | 604/82 |
| 7,740,607 B2 | * | 6/2010 | Willis et al. | 604/68 |

(Continued)

FOREIGN PATENT DOCUMENTS

| | | |
|---|---|---|
| DE | 102006041809 A1 | 3/2008 |
| WO | 8802265 A1 | 4/1988 |
| WO | 2004108205 A1 | 2/2004 |

*Primary Examiner* — Quynh-Nhu H Vu
(74) *Attorney, Agent, or Firm* — McDonnell Boehnen Hulbert & Berghoff LLP

(57) ABSTRACT

A medicated module (4) for an injection system to co-deliver at least two medicaments is disclosed where a primary delivery device containing a primary medicament accepts a medicated module (4) containing a single dose of a secondary medicament (2) and where both medicaments are delivered through a single hollow needle (5). The medicated module (4) is user selectable so that it will deliver both the primary (1) and secondary medicaments (2), or only the primary medicament (1). The module (4) also contains a guard (42) that locks after dose delivery.

13 Claims, 4 Drawing Sheets

(56) References Cited

U.S. PATENT DOCUMENTS

| | | | |
|---|---|---|---|
| 7,963,939 B2 * | 6/2011 | Chun | 604/88 |
| 8,251,947 B2 * | 8/2012 | KraMer et al. | 604/82 |
| 2001/0037087 A1 * | 11/2001 | Knauer | 604/137 |
| 2003/0055376 A1 * | 3/2003 | Delay | 604/82 |
| 2003/0093036 A1 * | 5/2003 | Crossman et al. | 604/197 |
| 2006/0036216 A1 * | 2/2006 | Rimlinger et al. | 604/198 |
| 2006/0229562 A1 | 10/2006 | Marsh et al. | |
| 2006/0276755 A1 | 12/2006 | Sullivan et al. | |
| 2008/0154200 A1 * | 6/2008 | Lesch | 604/135 |
| 2008/0221528 A1 | 9/2008 | Lanz | |
| 2009/0018506 A1 * | 1/2009 | Daily et al. | 604/136 |
| 2011/0282173 A1 * | 11/2011 | Fonduca et al. | 600/365 |

\* cited by examiner

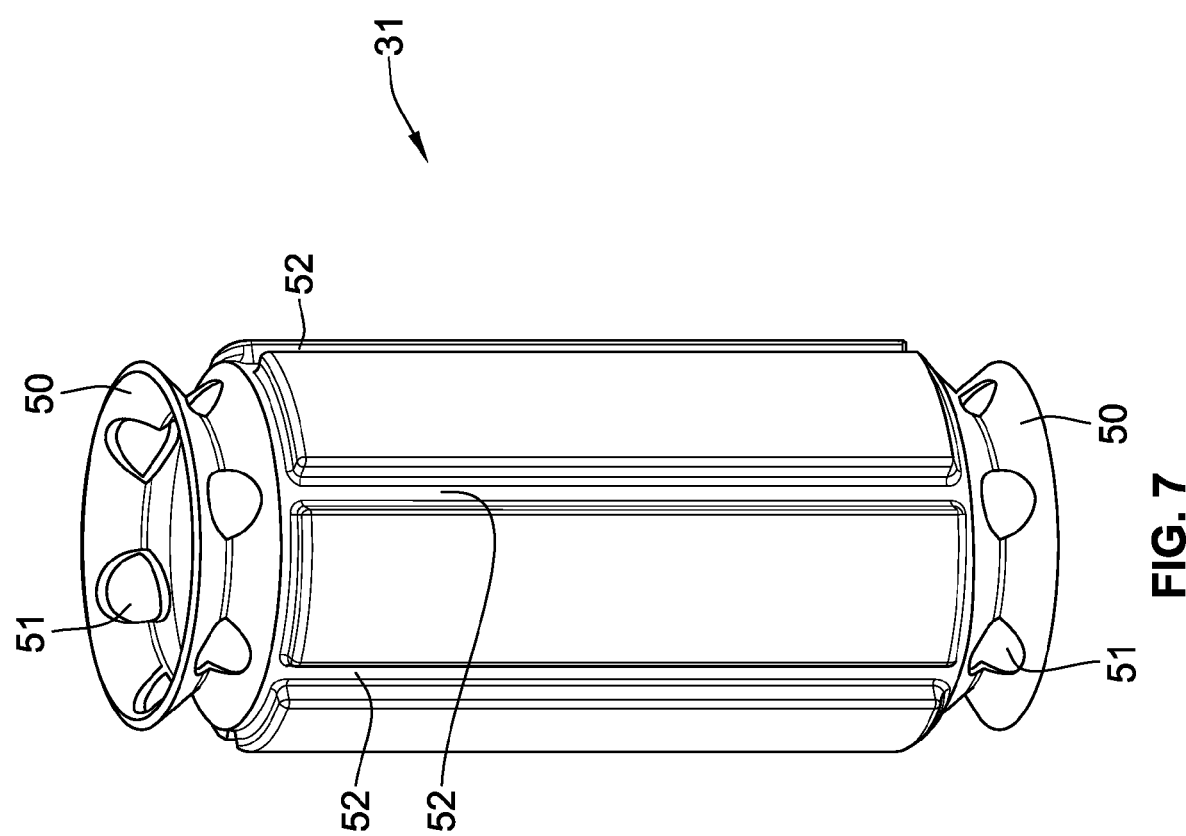

MEDICATED MODULE WITH USER SELECTION

CROSS REFERENCE TO RELATED APPLICATIONS

The present application is a 35 U.S.C. 371 National Application of PCT/EP2010/057579 filed Jun 1, 2010, which claims priority to U.S. Provisional Patent Application No. 61/183,459 filed Jun 2, 2009 and European Patent Application No. 09009661.1 filed Jul. 25, 2009, the entire contents of which are incorporated entirely herein by reference.

FIELD OF THE PRESENT PATENT APPLICATION

According to one aspect the present disclosure relates to medical devices and methods of delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. According to a specific aspect the disclosure concerns a medicated module where the user has to select whether to dispense the second drug agent or to bypass the second drug agent and only dispense the first drug agent. Our invention is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two or more active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more active agents may require a titration period to gradually introduce a patient up to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. According to one specific aspect, our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Our invention may also give the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

Our invention may also provide a medicated module that allows the user to select whether medicaments from two reservoirs are dispensed together or whether the secondary medicament in the module is bypassed to provide delivery of only one medicament either as a non-receivable (i.e. not able to inject) priming dose, or as a receivable/injected dose of only the one medicament.

These and other advantages will become evident from the following more detailed description of the invention.

Problem to be Solved

The general problem to be solved by the present invention is to provide a medicated module and drug delivery system where the administration of a medicament is improved.

SUMMARY

According to one aspect the present disclosure allows complex combinations of multiple drug compounds within a single drug delivery system. The invention may allow the user to set and dispense a multi-drug compound device through one single dose setting mechanism and a single dispense interface. This single dose setter may control the mechanism of the device such that a predefined combination of the individual drug compounds is delivered when a single dose of one of the medicaments is set and dispensed through the single dispense interface.

The term drug dispense interface preferably is, in the context of this disclosure, any type of outlet that allows the two or more medicaments to exit the drug delivery system and be delivered to the patient. In a preferred embodiment the single drug dispense interface comprises a hollow needle cannula.

For example, by defining the therapeutic relationship between the individual drug compounds our delivery device would help ensure that a patient/user receives the optimum therapeutic combination dose from a multi-drug compound device without the inherent risks associated with multiple inputs where the user has to calculate and set the correct dose combination every time they use the device. The combination of the individual medicaments comprises preferably at least two different drug agents, wherein each medicament comprises at least one drug agent. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

This invention may be of particular benefit to users with dexterity or computational difficulties as according to one specific aspect the single input and associated predefined therapeutic profile removes the need for them to calculate their prescribed dose every time they use the device and the single input allows considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. The secondary medicament may comprise a GLP-1 or a formulation comprising insulin and a GLP-1. When connected to the primary device the secondary compound is activated/delivered on dispense of the primary compound. Although according to some embodiments our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one embodiment, our invention relates to a medicated module attachable to a drug delivery device, for example a single dose or multi-dose drug delivery device. Preferably, the medicated module contains a liquid medicament. The medicated module may contain a GLP 1. The medicated module comprises a housing having a proximal end and a distal end, where the proximal end has a connector configured for attachment to a drug delivery device. The drug delivery device may house a primary reservoir containing at least one dose of a first medicament. The primary reservoir may contain multiple doses of the first medicament. The medicated module comprises a reservoir, in the following also called secondary reservoir, containing at least one dose of a medicament. The reservoir may contain only a single dose of the secondary medicament.

In one embodiment of our invention there is provided a medicated module attachable to a drug delivery device that comprises a housing having a proximal end, a distal end, and an outer surface, where the proximal end has a connector configured for attachment to a drug delivery device. A first needle may be fixed within the medicated module at the proximal end. A second needle may be fixed within the medicated module at the distal end or, according to a specific embodiment, may be fixed within a moveable needle hub. There is a reservoir in the housing that contains a medicament. The reservoir may be defined by a recess within the connecting body. The reservoir may alternatively be defined by a capsule, i.e. a self-contained sealed reservoir of the second medicament. The reservoir is configured for fluid communication with the first and the second needle. Preferably, the reservoir contains a single dose of the medicament. The module also contains a guard. The guard may serve as a needle guard that can reduce the risk of accidental needle sticks as well as reduce the anxiety of users suffering from needle phobia. The guard is preferably configured to move axially in both the distal and proximal directions when pressed against an injection site e.g. during application to an injection site. Preferably, when the module is removed or withdrawn from the patient, the guard is returned to its original starting location. In a preferred configuration, the guard will be locked from further axial movement. According to a specific embodiment the guard is operably connected to the housing.

Locking of the guard after axial movement can be accomplished in many ways that are known to those skilled in the art, however, a preferred method includes the use of a moving or sliding lock contained within the module. This moving lock is configured such that when the guard moves axially in the proximal direction it engages (picks up) the moving lock and then when the guard reverses direction (moving in the distal direction) it carries with it the moving lock. At a point when the guard has finished its reverse movement the moving lock becomes fixed or locked to a non-moving portion of the medicated module while remaining engaged to the guard. This prevents the guard from further axial movement in either direction.

The medicated module may also contain a selector suitable for adjusting the operation status of the module. According to a first aspect of the present disclosure, the operation status of the module depends on the status of the guard. In a first status, the guard may be moveable in axial direction whereas in a second status the guard may be locked. In order to adjust the status of the guard, the selector is operably connected to the guard. According to a second aspect of the present disclosure, the operation status of the module depends on the status of the reservoir. In a first status, the reservoir may be isolated and the medicament in the reservoir is not allowed to be dispensed, e.g. the reservoir may not be in fluid communication with a drug dispense interface, e.g. a needle cannula, whereas in a second status the reservoir is in fluid communication with the dispense interface such as a needle cannula and the medicament therein is allowed to be dispensed. In order to adjust the status of the reservoir, the selector is operably connected to the reservoir. According to a specific embodiment the status of the module depends on both the status of the guard and the status of the reservoir. In this case, the selector is operably connected to the reservoir as well as to the guard. The module may thus contain a selector that is operably connected to the guard in such a way that the user can move the selector, preferably by rotation, to allow the medicament in the reservoir, which in a preferred embodiment is a self-contained capsule, to be dispensed along with the primary medicament, or to allow a primary medicament to bypass the reservoir or to fulfill a priming function of a delivery device. Preferably the selector has a raised surface or protrusions projecting outwardly, or other like designed tactile features that allow the user to easily and conveniently move the selector to one of two, three, or more possible settings. The selector also has an indicator that shows the position or setting of the selector. Preferably, the indicator can be a pip, knob, button, or the like that protrudes through the outer surface of the housing and visually shows the user the position of the selector. It may also be a visual indicator, e.g. showing colors or symbols, or a tactile or audible indicator.

Preferably the selector can have two or three positions. The following description is for a three-position selector. A first setting could be where the guard is locked and thereby prevented from axial movement and the reservoir in the module is isolated, for example not in fluid communication with a needle cannula so that a primary medicament contained in a separate reservoir can be used to prime an attached delivery device using, for example, a bypass around or through or independent of the reservoir in the module. A second position or setting of the selector could allow the guard to move axially, e. g. during application/pressing the module to an injection site (whether or not the dose button is actually activated). Selection of this second position could cause the medicament in the module reservoir to come into fluid engagement with a dose dispense interface, such as a hollow needle cannula. The needle cannula may be mounted in the proximal end of the housing. A third position could also allow the needle guard to move axially, but not allow the medicament in the reservoir to be dispensed. In this possible third position, medicament from a primary reservoir located in an attached drug delivery device would bypass the module reservoir and be dispensed directly through the dose dispense interface. The module reservoir may contain a liquid medicament.

In another preferred configuration of our medicated module, the selector is operably connected to the module reservoir, which as mentioned is preferably a self-contained, sealed and sterile capsule containing a single dose of a second medicament. This second medicament can be the same or different from the first or primary medicament in the drug delivery device to which the medicated module is designed to be attached. Preferably the selector defines part of a cavity that holds the capsule, such that when the selector is moved by the user to a predetermined position (for example a first position) the cavity volume decreases causing the capsule to be pierced at its top and bottom by conduits that allow the medicament to be expelled from the capsule during dose delivery. Preferably the conduits are hollow needle cannulae mounted securely in the medicated module that are configured to pierce septa located on the top and bottom ends of the capsule. Prior to piercing the capsule the conduits are only in fluid communication with the top and bottom of the cavity to define a fluid flow path that bypasses the capsule. This fluid flow path or channel is used in the priming function of the delivery device and in delivery of only the primary medicament. This bypass could be achieved by a number of means designed such that the primary medicament could flow to the dispense interface without interacting with the medicament contained within the reservoir within the medicated module.

Our invention also relates to a drug delivery system to deliver two or more medicaments through a single dispense interface. The drug delivery system comprises a primary reservoir of medicament containing at least one drug agent and a dose button operably connected to the primary reservoir of medicament. The primary reservoir may comprise insulin. The drug delivery system may comprise, a housing. The system also has a single dispense interface configured for fluid communication with the primary reservoir and a medicated module. The medicated module is configured for fluid communication with the primary reservoir and comprises a proximal end and a distal end, where the proximal end has a connector configured for attachment to the housing of the drug delivery device. The module preferably has a sealed secondary reservoir containing a second medicament. Preferably the secondary reservoir contains a single dose of the second medicament. The module further comprises a guard configured to move in an axial direction when the module is applied to an injection site, and a selector for adjusting the operation status of the module. Preferably, the selector is operably connected to the primary reservoir. The selector is settable in two or more predetermined positions. With a single activation of the dose button medicament from the primary reservoir and the second medicament from the secondary reservoir can be expelled through the dispense interface when the selector is set to one of the predetermined positions. Alternatively, depending on the position of the selector as set by the user, only the primary medicament can be dispensed (or used to prime the system) and thus bypassing the secondary reservoir. The system may further be operable through a single dose setter which is operably connected to a primary reservoir and which may be contained in the housing. By means of the dose setter, a dose of the medicament of the primary reservoir may be set and thereafter dispensed on activation of the dose button. Preferably the dose setter is not operably connected to the second reservoir. As no further dose setters are available in this embodiment, regarding the second medicament a non-user settable dose is dispensed on activation of the dose button.

A further aspect of the invention relates to a method of dispensing a fixed dose of one medicament and a variable dose of a primary medicament from separate reservoirs that involves the steps of first attaching a medicated module to a delivery device having a selector that can be placed in a starting, second and third positions, or alternatively just a starting and a second position where starting is prime only and second is combination delivery. With the selector in the starting or first position, the user can prime the dose delivery device using only the primary medicament and bypassing the second medicament. After priming the user selects either the second or third position of the selector. If the user has not already set a dose of the first medicament, the user then sets a dose of a first medicament contained in a primary reservoir of the drug delivery device using a single dose setter. If the selector is set to the second position then when the user activates a dose button the set dose of the first medicament from the primary reservoir is caused to move in a distal direction and simultaneously forces substantially all of a non-user set dose (e.g. a single dose) of a second medicament from a secondary reservoir contained in a medicated module through a single dispense interface, preferably a hollow injection needle. The secondary reservoir may be a sealed capsule. Upon completion of the delivery procedure, substantially all of the second medicament has been expelled as well as the selected dose of the first medicament through the single dispense interface. By "substantially all" we mean that at least about 80% of the second medicament is expelled from the drug delivery device, preferably at least about 90% is expelled. On the other hand, if the selector is in the third position then the first medicament is forced into a bypass channel around the second reservoir in the medicated module and only the first medicament is dispensed. For bypassing purposes a fluid path may be defined in the cavity bypassing the capsule when the selector is in a first or third position. In either situation, it is preferred that a needle guard will prevent a second delivery or insertion through a locking mechanism as described previously.

The combination of compounds as discrete units or as a mixed unit is delivered to the body via an integral needle. This would provide a combination drug injection system that, from a user's perspective, would be achieved in a manner that very closely matches the currently available injection devices that use standard needles.

The medicated module of our invention can be designed for use with any drug delivery device with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A drug delivery device preferably comprises a primary reservoir of medicament containing at least one drug agent, a dose setter, a dose button, and a delivery mechanism. The dose button is operably connected to the primary reservoir. The dose setter is operably connected to the primary reservoir. The delivery mechanism may be of any type utilizing a rotatable piston rod, preferably a rotatable piston rod with two distinct threads. In a preferred embodiment, the dose button is operably connected to a spindle that engages a piston in the primary reservoir of the first medicament. In a further embodiment the spindle is a rotatable piston rod comprising two distinct threads.

A particular benefit of our invention is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of our invention, the primary drug delivery device is used more than once and therefore is multi-use, however, the drug delivery device may also be a single use disposable device. Such a device may or may not have a replaceable reservoir of the primary drug compound, but our invention is equally applicable to both scenarios. It is also possible to have a suite of different medicated modules for various conditions that could be prescribed as one-off extra medication to patients already using a standard drug delivery device. Should the patient attempt to reuse a previously used medicated module, our invention includes the locking needle guard that is activated after drug dispense or insertion that could alert the patient to this situation. Other means of alerting the user may include some (or all) of the following:

1. Physical prevention of medicated module re-attachment to the primary drug deliver device once the module has been used and removed.
2. Physical/hydraulic prevention of subsequent liquid flow through the drug dispense interface once it has been used.
3. Physical locking of the dose setter and/or dose button of the primary drug delivery device.
4. Visual warnings (e.g. change in color and/or warning text/indicia within an indication window on the module once insertion and/or fluid flow has occurred).
5. Tactile feedback (presence or absence of tactile features on the outer surface of the module hub following use).

A further feature of this embodiment is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

Our invention also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 5 B illustrate a sectioned view of one embodiment of the invention when the selector is set to a second position with the medicated module reservoir engaged and where the guard is moved axially to engage a moving lock; and with a locked guard.

FIG. 5 C illustrate a sectioned view of one embodiment of the invention when the selector is set to a second position with the medicated module reservoir engaged and where the guard has reversed axial direction and is locked from further axial movement.

FIG. 7 illustrates a capsule with bellow type support structure and bypass vanes.

DETAILED DESCRIPTION

Figures 1, 6:
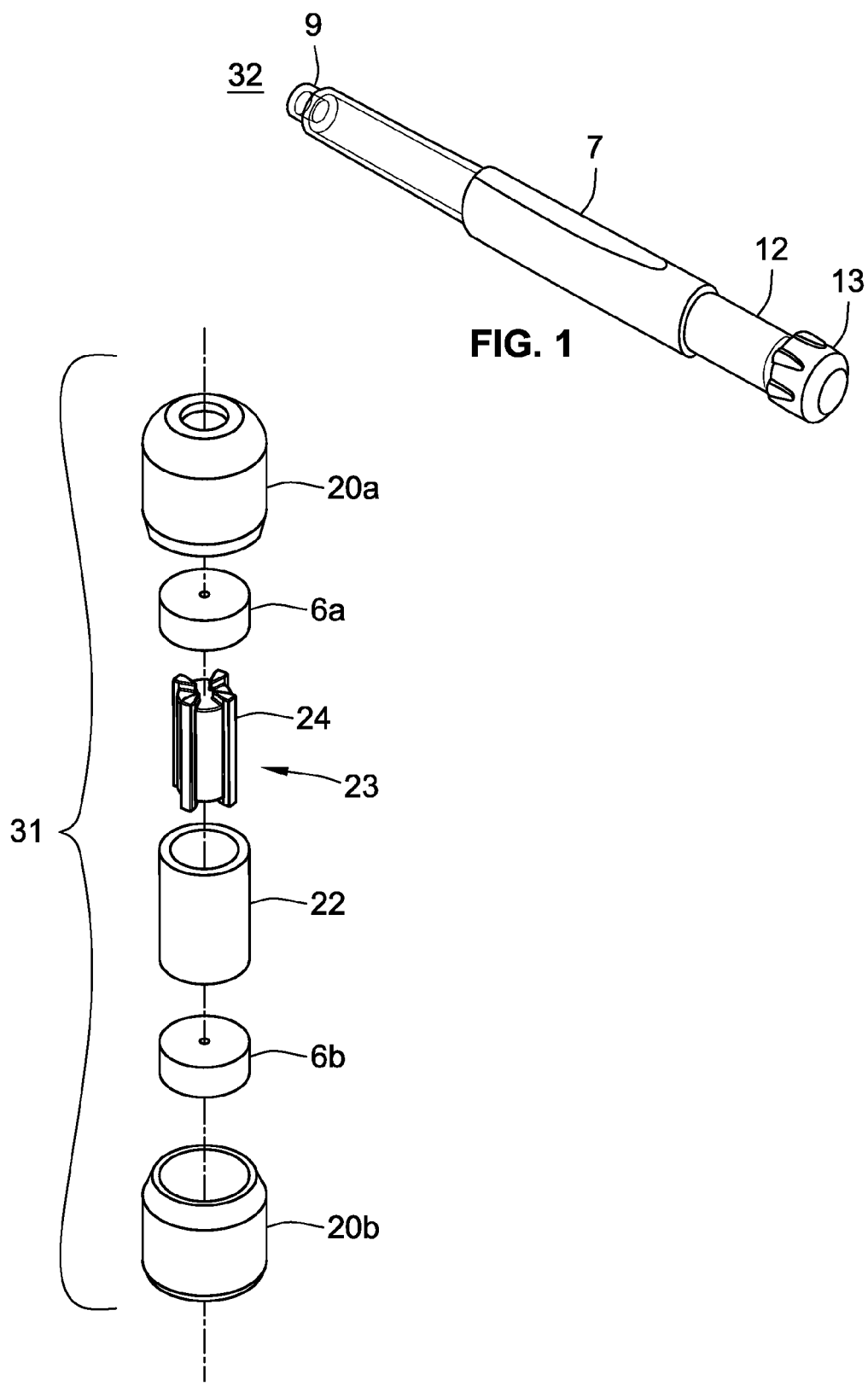
FIG. 1 illustrates one possible drug delivery device that can be used with the present invention.
FIG. 6 illustrates a disassembled embodiment of the capsule of the present invention having an annular flow distributor.
Figure 2:
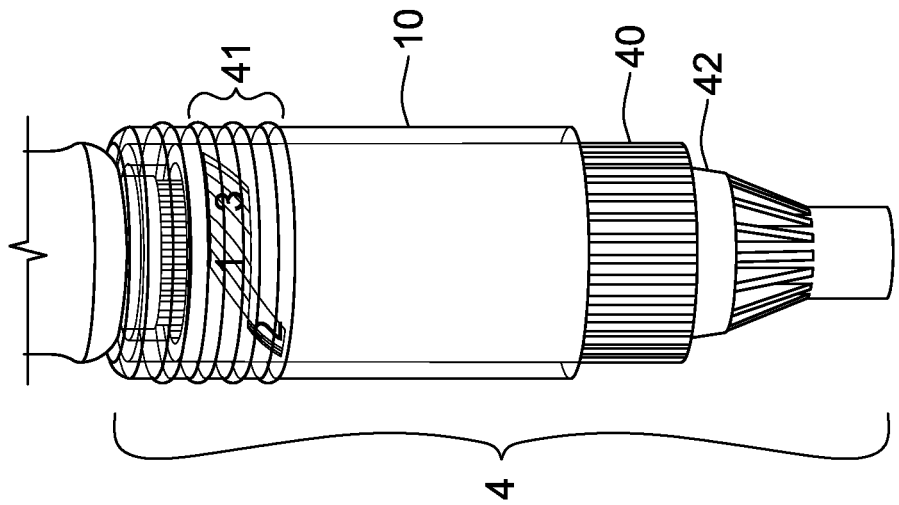
FIG. 2 illustrates an embodiment of the medicated module of the present invention having a user settable selector feature, where the medicated module is attached to a drug delivery device.

According to a preferred embodiment, the present disclosed apparatus administers a fixed predetermined dose of a secondary drug compound (medicament) and a variable dose of a primary or first drug compound through a single output or drug dispense interface. Setting the dose of the primary medicament by the user automatically determines the fixed dose of the second medicament, which preferably is a single dose contained in a capsule having an integral flow distributor. In a preferred embodiment the drug dispense interface is a needle cannula (hollow needle). FIG. 1 illustrates one example of a drug delivery device 7 that the medicated module 4 (see FIGS. 2-3) of our invention can be attached to the connection means 9 of distal end 32. Each medicated module is preferably self-contained and provided as a sealed and sterile disposable module that has an attachment means 8 compatible to the attachment means 9 at the distal end 32 of device 7. Although not shown, the medicated module could be supplied by a manufacturer contained in a protective and sterile container, where the user would peel or rip open a seal or the container itself to gain access to the sterile medicated module.

In some instances it might be desirable to provide two or more seals for each end of the medicated module.

Any known attachment means 8 can be used to attach the medicated module to the chosen drug delivery device, including all types of permanent and removable connection means, such as threads, snap locks, snap fits, luer locks, bayonet, snap rings, keyed slots, and combinations of such connections. FIGS. 2-5 illustrate the attachment means 8 as a snap fit that would engage a rib or possibly threads as an example of connection means 9 of the distal end 32 of drug delivery device 7. The embodiments shown in FIGS. 2-5 have the benefit of the second medicament 2 as a single dose being contained entirely within capsule 31, hence minimizing the risk of material incompatibility between the second medicament and the materials used in the construction of the medicated module 4, specifically housing 10 or any of the other parts used in the construction of the module.

To minimize the residual volume of the second medicament, caused by recirculation and/or stagnant zones, that might remain in capsule 31 at the end of the dispense operation, it is preferable to have a flow distributor 23 contained within vial 22 portion of capsule 31 (see FIG. 6). The vial, secondary medicament and flow distributor can be sealed with top and bottom septa 6a and 6b, which are fixed to the capsule using ferules 20a and 20b, however, any type of seal could be used. Preferably the ferules are made from a crimpable material, most preferably a metal, such as aluminum. Preferably, the design of flow distributor 23 should ensure that at least about 80% of the second medicament is expelled from capsule 31 through the distal end of needle 3. Most preferably at least about 90% should be expelled. Ideally displacement of the first medicament 1 from the primary reservoir 11 through the capsule 31 will displace the second medicament 2 without substantial mixing of the two medicaments.

Attachment of the medicated module 4 to the multi-use drug delivery device 7 causes the engagement needle 5 located in the proximal end of module 4 to penetrate a septum (not shown) sealing the distal end of cartridge 11 of the multi-use device 7. Once the engagement needle has passed through the septum of the cartridge, fluid connection is made between the first medicament 1 and the needle 5. At this point the system can be primed or the dose of the multi-use device 7 set using a dose setter 12 (see FIG. 1) in the normal manner (e.g. by dialing out the appropriate number of units or cocking the device if only a single dose is possible). If the selector 40 is set to the second position, the dispense of both, the first and the second medicament is then achieved by subcutaneously injecting the medicaments via activation of a dose button 13 on device 7. The dose button according to the invention can be any triggering mechanism that causes the dose of the first medicament that was set by the dose setter to move towards the distal end 32 of the device. In a preferred embodiment the dose button is operably connected to a spindle that engages a piston in the primary reservoir of the first medicament. In a further embodiment the spindle is a rotatable piston rod preferably comprising two distinct threads.

One embodiment of our invention the medicated module 4 is illustrated in FIGS. 2-5. In these embodiments the medicated module 4 contains a discrete secondary reservoir or capsule 31 containing a fixed single dose of a secondary medicament 2. In some cases this secondary medicament may be a mixture of two or more drug agents that can be the same or different from the primary drug compound 1 in the drug delivery device 7. Preferably the capsule is permanently fixed contained within the medicated module and is designed to administer a fixed predetermined dose of a second medicament, however, in some cases it may be preferred to design the module such that the capsule can be removed when empty and replaced with a new capsule.

In the embodiments shown in FIGS. 2-5, capsule 31 has ends that are sealed with pierceable membranes or septa 6a and 6b that provide a hermetically sealed and sterile reservoir for the second medicament 2. A primary or engagement needle 5 can be fixed in the housing 10 of the module and configured to engage capsule 31 when selector 40 is moved to a predetermined position as described below. The output needle 3 is preferably mounted in selector 40 and initially protrudes above the lower surface of capsule 31. The proximal end of needle 3 pierces the lower membrane 6b when the volume of cavity 43 is decreased as the selector is moved to a predetermined setting.

Figure 3:
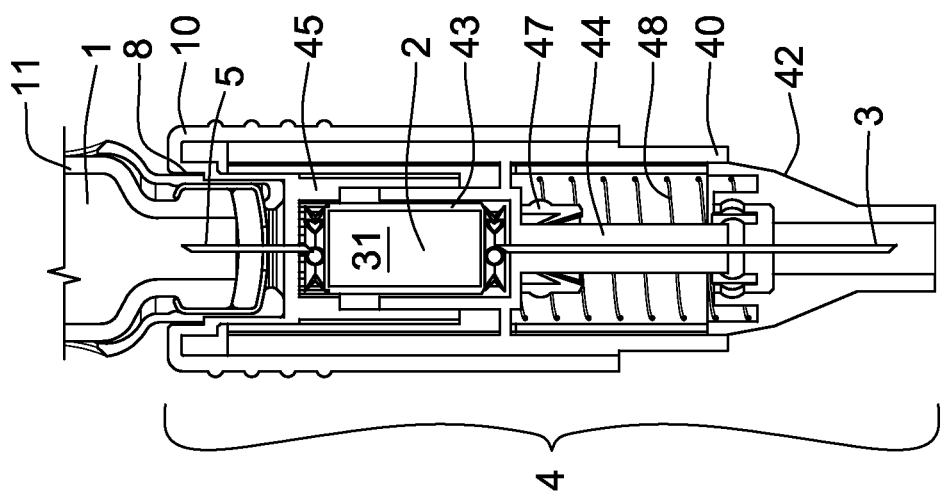
FIG. 3 illustrates a sectioned view of the embodiment of the medicated module shown in FIG. 2 orientated in the bypass configuration.

During use, attachment of the medicated module to a multi-use drug delivery device, such as the one shown in FIG. 1, the primary needle 5 pierces a septum of cartridge 11 contained in device 7. When first attached to a delivery device the medicated module selector 40 is set at a neutral, starting or position 1 as shown by indicator 41. The selector preferably is a tubular component positioned inside housing 10 and partially defining an internal cavity 43 that holds capsule 31. Needle 3 can be mounted in a portion of the distal end 44 of selector 40. A top portion of cavity 43 is defined by a portion of the proximal end of housing 10. FIG. 3 shows a cutaway view of the medicated module attached to a delivery device where the selector is positioned in a first, starting or neutral position. In this neutral position, the cavity 43 is at its largest volume and needles 3 and 5 are not in fluid communication with medicament 2 contained in capsule 31. FIG. 7 illustrates one possible design of capsule support features 50. These capsule supports may be bellow type structures having holes 51. The bellow structures keep the capsule suspended in the cavity avoiding penetration by needles 3 and 5 until required. In this non-collapsed or suspended state first medicament can flow from needle 5 through holes 51, around vial 22, back through holes 51, and out needle 3. When the volume of the cavity is decreased, the bellows 50 collapse, allowing the needles to pierce the septa. Alternatively, the capsule supports could be made part of housing 10, selector 40, or ferrules 20a/20b. Flow around or bypassing vial 22 is accomplished by configuring the capsule to have one or more vanes or channels 52 down the outside of the vial. Alternatively, housing or internal walls of the cavity could have these vanes or fluid channels incorporated therein and then the outer walls of the vial could be smooth.

Figure 4:
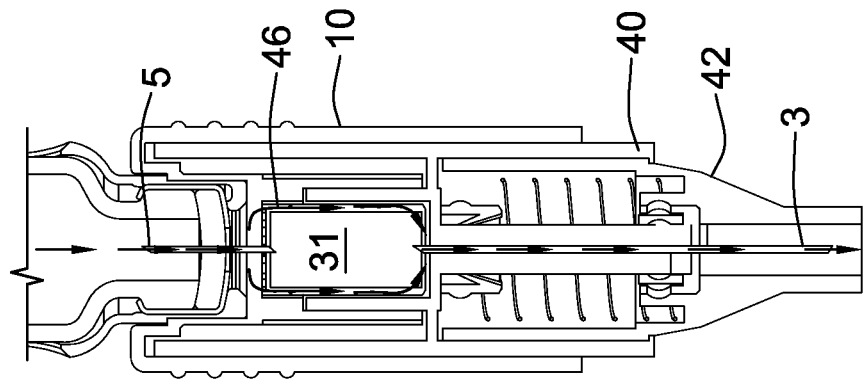
FIG. 4 shows the flow path of the primary medicament during priming or, if the needle guard is able to move axially, dispensing of the primary medicament only.

Needle 5, however, is in fluid communication with primary medicament 1 in cartridge 11 as a result of the module being attached to the delivery device 7. Needle guard 42 is locked to prevent axial movement when selector 40 is in the first or starting position. When a two-position selector is used, then the guard in the start position would not be locked. If desired, the user could perform a priming step or procedure as illustrated in FIG. 4 by setting a small dose of the primary medicament 1 using the dose setter 12 and dose button 13 on the drug delivery device 7. Directional arrows 46 show the flow of the small dose of primary medicament 1 flowing from cartridge 11 through needle 5 around or bypassing capsule 31 and exiting needle 3. This same flow path of primary medicament 1 would occur if the user set the selector to a third position 3, set a prescribed dose of medicament 1, and injected/dispensed that dose.

As mentioned, when the selector 40 is in the neutral or starting position, the needle guard 42 is locked and thus needle 3 is inaccessible to an injection site and the user is unable to deliver a dose of either medicament 1 or medicaments 1 and 2. If the selector is moved to a third position (see FIG. 2 where indicator 41 shows a position 3), the guard 42 becomes unlocked and is free to travel in an axial proximal direction thus exposing needle 3 and allowing the user to administer a dose of medicament 1, but not medicament 2 in capsule 31. This is because moving the selector from position 1 to position 3 does not change the volume in cavity 43 and therefore does not cause the capsule to become fluidly engaged with needles 3 and 5. In other words, the disposition of the capsule is the same when the selector is in either position 1 or position 3. In position 3 the user can prime the system with medicament 1, as shown in FIG. 4, and the user can deliver a dose of medicament 1 by placing the guard on the dose delivery site and pushing it axially to move the guard in the proximal direction to expose the distal end of needle 3. Priming is possible because the cavity 43 is large enough to define a fluid channel around capsule 31 so that medicament 1 can flow around or bypass the capsule and exit direct through needle 3. In some cases it may be beneficial to include in the selector locking features that prevent the user from de-selecting a selected position. This lock-out feature can be accomplished in a variety of ways, including non-reversible detents or snap-locks.

The guard or safety shield 42 could be any design that would prevent accidental needle sticks and/or reduce the anxiety experienced by users who suffer from needle phobia. The exact design of the safety shield is not critical to our invention, however, a preferred design, as disclosed below, is one that prevents only a singe dose delivery to a user (or use of needle 3) regardless of whether the selector is in the second or third position. Preferably, the needle guard is locked from axial movement when the selector is in the starting or position 1.

During dose delivery, when the selector is in position 2 or 3, the guard 42 moves or slides proximally relative to housing 10. Proximal movement of the guard 42 activates or loads a resilient or biasing member within the module housing, which preferably could be a compression spring 48 or a set of one or more flexible arms. As the guard reaches a trigger point in its proximal travel, it engages or picks up a sliding lock 47. The trigger point could be any point along the travel, preferably at the end of travel. For safety reasons, moving the trigger point to earlier in the travel could be beneficial to ensure that the locking system is triggered as soon as the needle tip penetrates the patient. Upon completion of the dose delivery and upon withdrawing the module from the patient's injection site, the guard 42 will reverse its axial path moving distally due to the force or reverse action of the resilient member (e.g. spring 48). As the guard moves distally it will carry a moving or sliding lock 47 with it until the lock engages a non-moving part of the medicated module 4. When so engaged, as shown in FIG. 5C, the guard will then be prevented from moving axially preventing re-use of needle 3 and will cover the needle to prevent accidental needle sticks. Although a specific design of the moving lock is illustrated in FIGS. 2-5, any type of lock, whether moving or not, will work on our invention, for example a sliding o-ring or stationary flexible fingers or single use "retractable biro pen" type mechanism or pin following a groove could be used as long as the guard is locked in a needle covering position and prevents further use of the medicated module as a dose delivery tool.

Figure 5A:
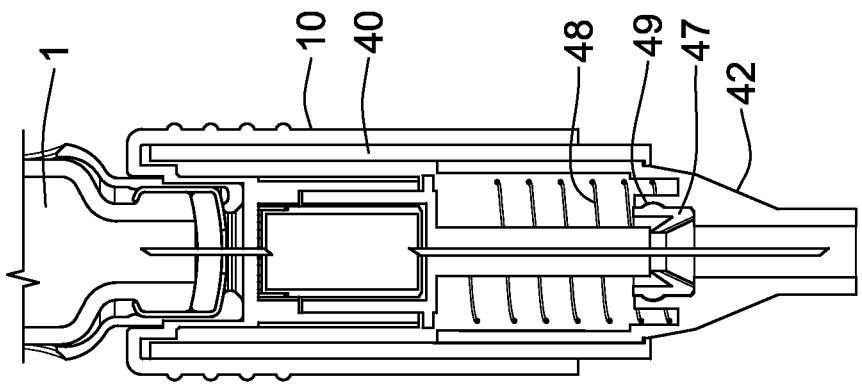
FIG. 5 A illustrate a sectioned view of one embodiment of the invention when the selector is set to a second position with the medicated module reservoir engaged and where the guard is unlocked.
Figure 5B:
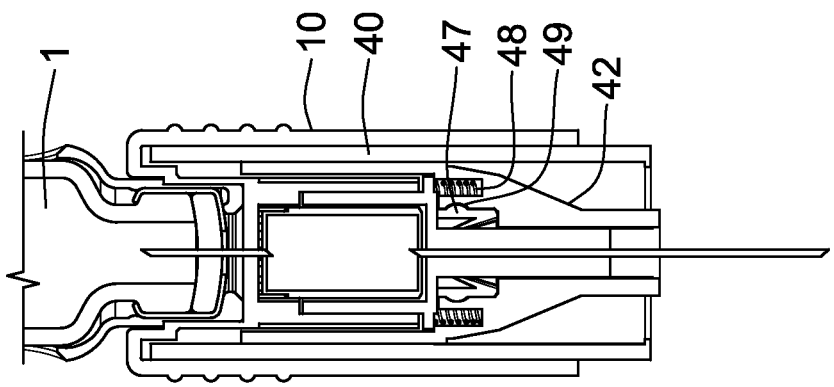
Figure 5C:
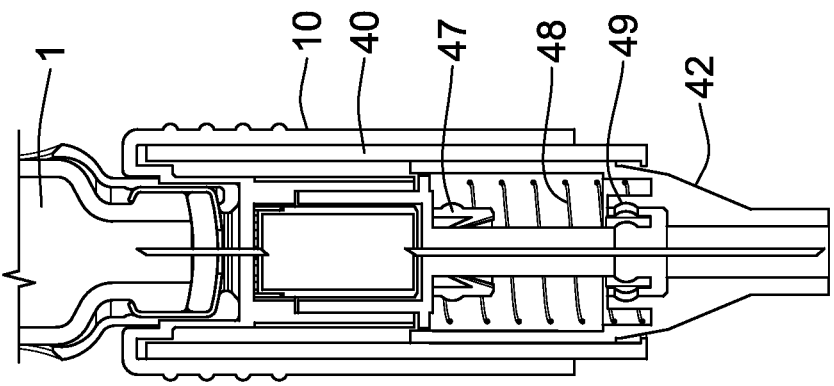

FIGS. 5A-5C illustrate the medicated module when the selector 40 is set to position 2. In this position the selector has moved axially in the proximal direction and has decreased the volume of cavity 43. As the volume of cavity 43 is decreased, capsule 31 is likewise moved axially in the proximal direction forcing engagement of septa 6a and 6b with needles 5 and 3, respectively, thus creating fluid engagement between medicament 1, needle 5, medicament 2, and needle 3: As the volume of cavity 43 is decreased, capsule 31 moves axially in proximal direction forcing engagement of proximal septum 6a with needle 5 thus creating fluid engagement between medicament 1 and needle 5; furthermore as the volume of cavity 43 is decreased, engagement of needle 3 with distal septum 6b is forced, thus creating a fluid engagement between medicament 2 and needle 3; consequently creating fluid engagement between medicament 1, needle 5, medicament 2, and needle 3. This initial engagement with the capsule 31 and needles 3 and 5 is shown in FIG. 5A. At this point, with the selector set to position 2, the guard is unlocked and able to move proximally to expose needle 3 for dose delivery. However, because needles 3 and 5 are in fluid engagement with medicament 2, the system cannot be primed without accidentally losing or wasting medicament 2. Additionally, because the volume of cavity 43 has been decreased when the selector was moved to the second position, the bypass fluid channel used for priming is lost or no longer useable. FIGS. 5B and 5C show the dose delivery positions (during delivery/needle guard displacement and after) of the module when the selector is in the second position. FIG. 5 C shows that locking member 47 was picked-up from a first position (see FIG. 5B) by engaging grove 49 in the guard and brought to a second position (see FIG. 5C) where it locks with the distal end 44 of selector 40. The movement and locking of the guard is the same when the selector is in either the second or third positions.

In any of the above described embodiments of our invention the second medicament may be either in a powdered solid state, any fluid state contained within the secondary reservoir or capsule, or coated to the inside surface of the drug dispense interface. In particular, the secondary reservoir may contain a liquid medicament. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

In any of the above embodiments the third position could be removed such that the system only has two positions: first where the needle guard is locked and the bypass is engaged. In this default state the user is prompted to prime the device but cannot inject the dispensed fluid from the primary reservoir. The second position is that in which the capsule is engaged and the needle guard is unlocked. The user receives the combination dose and the needle guard locks out after removal from the injection site. This is a basic version of the preferred embodiment used where it is not desirable to offer the "primary medicament only" selection to the user, but still prompting them to select the combination dose in order to deliver it.

To minimize diffusion of the secondary medicament contained in the capsule within the medicated module into the primary medicament during dispense of the medicaments a flow distributor is included in the capsule. This flow distributor also ensures efficient expulsion of the second medicament from the system and greatly minimizes residual volume. One possible embodiment of the flow distributor is illustrated in FIG. 6 as an annular pin. Annular pin 23 is positioned in vial 22 and configured such that the secondary medicament fills flow channels that are defined by the shape and location of two or more support ribs 24. The flow distributor (annular pin) can be constructed of any material that is compatible to the primary and secondary medicaments. A preferred material would be that typically used to manufacture septa or pistons (bungs) found in multi-dose medicament cartridges, although any material that is compatible with the medicament during long term storage would be equally applicable. The shape of the flow channels can be optimized for a plug flow of medicament by varying the dimensions and number of support ribs 24. The cross-sectional area of the annulus formed between the flow distributor and the wall of the vial should be kept relatively small. The volume available to store the secondary medicament would equal the internal volume of the capsule minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. A further benefit of this is that as the available volume for medicament is defined by the difference in volumes between the flow distributor and its housing, the external capsule geometry is not dictated by the volume of medicament. Resultantly for small volumes of secondary medicament (e.g. 50 micro liters) the capsule can be of an acceptable size for handling, transport, manufacture, filling and assembly.

The connection or attachment between the medicated module of the above descried embodiments may contain additional features (not shown), such as connectors, stops, splines, ribs, grooves, and the like design features, that ensure that specific medicated module are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the secondary medicament and for attaching one or more needle cannula. The secondary reservoir can be manufactured from glass or other drug contact suitable material. The integrated injection needle can be any needle cannula suitable for subcutaneous or intramuscular injection.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of our invention should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

In certain embodiments where the medicated module contains a single dose of a medicament, the module must be attached to a drug delivery device in order to administer the single dose in the reservoir to a patient. In other words, the medicated module cannot be used as a stand-alone injection device. This is because the module does not have a dose delivery mechanism and instead relies on the dose delivery mechanism contained in the drug delivery device to which it must be attached.

Exemplary embodiments of the present invention have been described. Those skilled in the art will understand, however, that changes and modifications may be made to these embodiments without departing from the true scope and spirit of the present invention, which is defined by the claims.

List of References
1 first medicament, primary medicament, medicament
2 second medicament, secondary medicament, medicament
3 needle, output needle
4 medicated module
5 needle, engagement needle, primary needle
6a, 6b septa
7 drug delivery device, device
8 attachment means
9 threads, connection means
10 housing
11 cartridge, primary reservoir
12 dose setter
13 dose button
20a, 20b ferrules
22 vial
23 annular pin, flow distributor
24 ribs
31 capsule, reservoir, secondary reservoir
32 distal end
40 selector
41 indicator
42 guard, needle guard, safety shield
43 cavity
44 distal end
46 directional arrows
47 sliding lock
48 compression spring
49 groove
50 bellows, support features
51 holes
52 channels, vanes

We claim:

1. A medicated module attachable to a drug delivery device, comprising,
   a. a housing having a proximal end and a distal end, where the proximal end has a connector configured for attachment to a drug delivery device;
   b. a reservoir in the housing comprising a first medicament;
   c. a guard configured to move in an axial direction during application to an injection site and arranged to serve as a needle guard that can reduce the risk of accidental needle sticks; and
   d. a moveable selector
   wherein the selector is operably connected to the guard such that the selector is moveable to two or more predetermined positions, said positions comprising:
   a first position where the guard is prevented from moving axially and the first medicament in the reservoir is not allowed to be dispensed, and
   a second position where the guard is free to move axially and the first medicament in the reservoir is allowed to be dispensed.

2. The medicated module of claim 1 where the selector has one or more tactile features accessible to a user to allow movement of the selector.

3. The medicated module of claim 1 where the selector is operably connected to the reservoir.

4. The medicated module of claim 1 where the selector positions comprise,
   a. a third position where the guard is free to move axially and the medicament in the reservoir is not allowed to be dispensed.

5. The medicated module of claim 4 where a fluid path is defined in the cavity bypassing the capsule when the selector is in a first or third position.

6. The medicated module of claim 1 where the guard is prevented from moving axially after dispensing the medicament from the reservoir.

7. The medicated module of claim 6 further comprising a moving lock configured to engage a stationary portion of the module when the guard moves axially.

8. The medicated module of claim 1 where a portion of the proximal end of the housing and a portion of the selector define a cavity for holding the reservoir, where the cavity has a proximal end and a distal end.

9. The medicated module of claim 8 where the proximal and distal ends of the cavity each are in fluid communication with a first and a second needle cannula.

10. The medicated module of claim 9 where the reservoir is a capsule.

11. The medicated module of claim 10 where the capsule is in fluid communication with the first and second needle cannula when the selector is in a second position.

12. The medicated module of claim 10 where the capsule is not in fluid communication with the first or second needle cannula when the selector is in the first or third position.

13. The medicated module of claim 1 where the reservoir contains a single dose of a medicament.

* * * * *